(12) United States Patent
Schuele et al.

(10) Patent No.: US 12,201,482 B2
(45) Date of Patent: Jan. 21, 2025

(54) STABILIZATION ASSEMBLY FOR HEAD FIXATION DEVICE

(71) Applicant: pro med instruments GmbH, Freiburg Im Breisgau (DE)

(72) Inventors: Matthias E. Schuele, Freiburg (DE); Sascha Kubis, Freiburg (DE); Marco S. Willesch, Eichstetten (DE); Peter Forst, Emmendingen (DE); Dirk H. Janz, Freiburg (DE)

(73) Assignee: pro med instruments, GmbH, Freiburg Im Breisgau (DE)

( * ) Notice: Subject to any disclaimer, the term of this patent is extended or adjusted under 35 U.S.C. 154(b) by 750 days.

(21) Appl. No.: 16/929,159

(22) Filed: Jul. 15, 2020

(65) Prior Publication Data

US 2021/0015580 A1  Jan. 21, 2021

Related U.S. Application Data

(60) Provisional application No. 62/874,026, filed on Jul. 15, 2019.

(51) Int. Cl.
*A61B 90/00* (2016.01)
*A61B 90/14* (2016.01)
*A61B 90/50* (2016.01)
*A61B 90/57* (2016.01)

(52) U.S. Cl.
CPC .............. *A61B 90/14* (2016.02); *A61B 90/50* (2016.02); *A61B 2090/571* (2016.02)

(58) Field of Classification Search
CPC ... A61B 2090/571; A61B 90/14; A61B 90/16; A61B 90/17; A61B 90/18; A61B 90/50; A61B 90/57; A61B 90/25; A61B 90/11; A61B 90/30; A61B 5/6814; A61G 13/121; A61G 13/101; A61G 13/10
USPC ......................................................... 128/845
See application file for complete search history.

(56) References Cited

U.S. PATENT DOCUMENTS

| | | | | |
|---|---|---|---|---|
| 2,932,867 | A | * | 4/1960 | Douglass, Jr. ......... A61G 13/12 24/524 |
| 2,998,954 | A | * | 9/1961 | Douglass, Jr. ......... A61G 13/10 248/316.2 |
| 3,835,861 | A | * | 9/1974 | Kees, Jr. ................. A61B 90/14 403/80 |
| 4,169,478 | A | * | 10/1979 | Hickmann ............. A61B 90/14 606/151 |

(Continued)

OTHER PUBLICATIONS

International Search Report and Written Opinion dated Dec. 8, 2020 for International PCT Application No. PCT/IB2020/000587, 19 pgs.

*Primary Examiner* — Adam Baker
(74) *Attorney, Agent, or Firm* — Frost Brown Todd LLP

(57) ABSTRACT

A head fixation device includes a rocker arm assembly containing one or more stabilizing features. The rocker arm is rotatably adjustable about a longitudinal axis of the rocker arm assembly to any rotational position in a non-stepped fashion. The rocker arm assembly is removable from the head fixation device for easy of cleaning. A lever of the rocker arm assembly translates a shaft and includes eccentric features to provide a camming action for moving locking features of the rocker arm assembly to an unlocked state such that the rocker arm can be rotationally adjusted.

20 Claims, 10 Drawing Sheets

(56) References Cited

U.S. PATENT DOCUMENTS

| | | | | |
|---|---|---|---|---|
| 4,547,092 | A | * | 10/1985 | Vetter .................. F16B 2/04 |
| | | | | 248/229.11 |
| 5,254,079 | A | * | 10/1993 | Agbodoe ............. A61B 90/14 |
| | | | | 602/32 |
| 5,269,034 | A | | 12/1993 | Day et al. |
| 5,897,087 | A | * | 4/1999 | Farley ................. A61B 90/50 |
| | | | | 248/316.2 |
| 9,402,692 | B2 | | 8/2016 | Schuele |
| 2001/0029379 | A1 | | 10/2001 | Grotehuis et al. |
| 2005/0075650 | A1 | | 4/2005 | Dinkler |
| 2008/0072381 | A1 | * | 3/2008 | Rolfes ................. A61B 90/14 |
| | | | | 5/637 |
| 2010/0059064 | A1 | | 3/2010 | Schuele et al. |
| 2014/0276823 | A1 | | 9/2014 | Schuele |
| 2017/0265894 | A1 | * | 9/2017 | Mark .................. A61B 90/50 |

* cited by examiner

STABILIZATION ASSEMBLY FOR HEAD FIXATION DEVICE

PRIORITY

This application claims priority to U.S. Provisional Patent Application Ser. No. 62/874,026, filed Jul. 15, 2019, entitled "Stabilization Assembly for Head Fixation Device," the disclosure of which is incorporated by reference herein.

BACKGROUND

The devices and methods disclosed pertain to patient stabilization, and in particular head and neck stabilization using stabilization devices known as head stabilization devices, which are also referred to as head fixation devices (hereinafter referred to as "HFDs" or "HFD" in singular). HFDs are sometimes used during a variety of surgical and other medical procedures, for example during head or neck surgery or testing where it would be desirable to securely hold a patient's head in a certain position. When stabilizing a patient's head, techniques include invasive and non-invasive setups. Invasive setups can use stabilizing features in the form of pins that contact the patient's head and in particular skull. Non-invasive setups can use stabilizing features in the form of pads or other structures that are configured to contact the patient's head but without penetrating the skin. HFDs used with invasive and non-invasive setups include structures or assemblies that are configured to retain and position one or more stabilizing features. While a variety of stabilization devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements.

Figure 1:
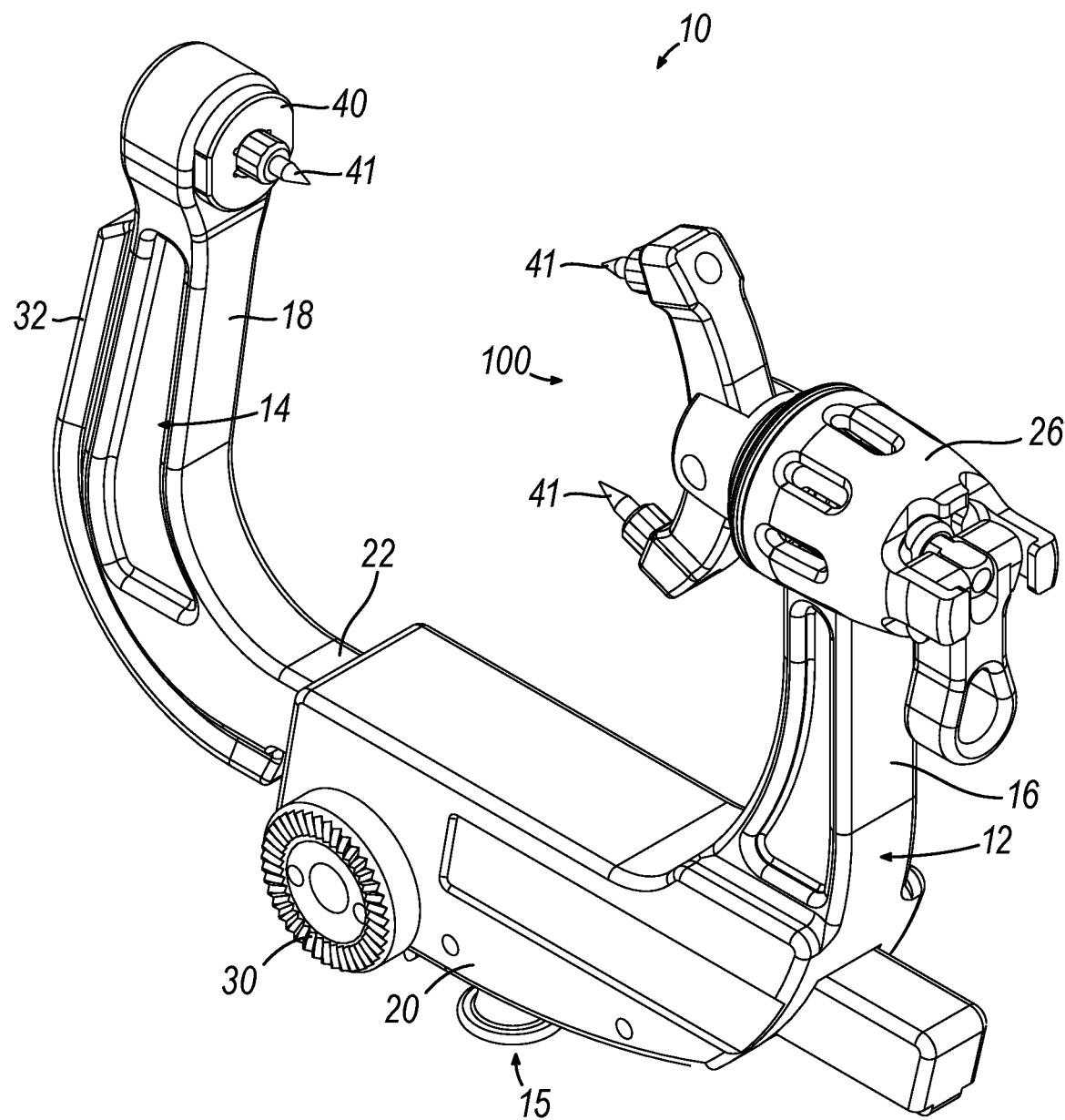
FIG. 1 depicts a perspective view of an exemplary HFD in the form of a skull clamp.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary HFD

FIG. 1 illustrates an exemplary head fixation device in the form of a skull clamp (10). Skull clamp (10) includes a first arm (12) that selectively connects with a second arm (14). First arm (12) and second arm (14) include respective upright portions (16, 18) and lateral portions (20, 22). One of lateral portions (20, 22), or both lateral portions (20, 22) collectively, may also be referred to as a base of skull clamp (10). First arm (12) and second arm (14) are adjustable to change the distance between arms (12, 14) to accommodate patients of various head sizes. A locking assembly (15) selectively connects lateral portions (20, 22) to permit such adjustment and secure arms (12, 14) relative to one another when a desired size change has been made.

Figure 8:
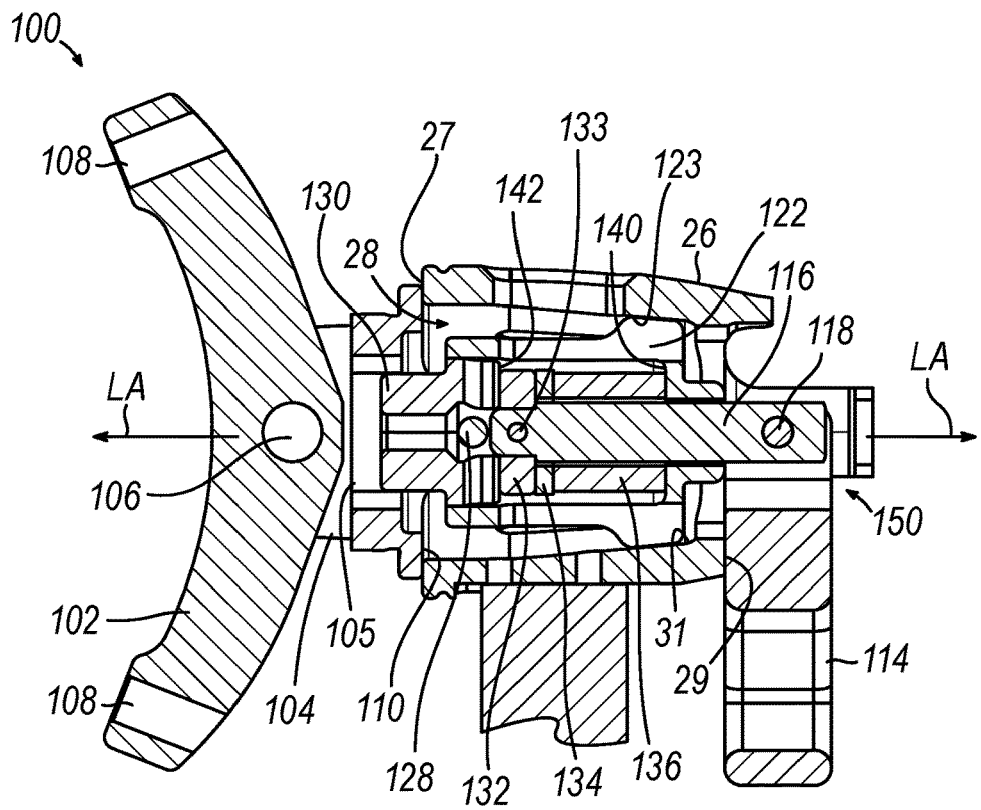
FIG. 8 depicts a side view in cross section of the rocker arm assembly of FIG. 2 connectable with the HFD of FIG. 1.

In the present example, upright portion (18) includes a bore (24) configured to receive an assembly (40) to hold a stabilizing feature (41). Stabilizing features retained with skull clamp (10) are in the form of skull pins in some versions, and in other versions are in the form of pads or other non-invasive structures. Upright portion (16) connects with a housing (26), and as will be described in further detail below, housing (26) is configured with a bore (28) as best seen in FIG. 8, and selectively receives a rocker arm assembly (100) as will be described in detail below. Rocker arm assembly (100) is configured to hold one or more stabilizing features (41), again which may be in the form of skull pins or in other versions in the form of pads or other non-invasive structures. Exemplary skull pins or non-invasive pads are available from pro med instruments GmbH of Freiburg, Germany.

Skull clamp (10) includes an attachment interface in the form of a starburst interface (30) in the illustrated version. In the present example, starburst interface (30) is configured to directly or indirectly connect skull clamp (10) with a patient support table (not shown). In some examples a swivel adapter, base unit, or combination thereof can be used to connect with starburst interface (30) to join skull clamp (10) with the patient support table. Exemplary swivel adapters and base units are also available from pro med instruments GmbH of Freiburg, Germany.

Skull clamp (10) further includes an attachment interface in the form of a rail (32) configured to receive a clamp member of other accessories for use with skull clamp (10). While in the present example, rail (32) is located on one side of skull clamp (10), in other versions rail (32) can be on the other side of skull clamp (10) or on both sides. Exemplary attachment interfaces in the form of a rail such as rail (32) are described further in U.S. Pat. No. 9,402,692, entitled "Head Fixation Device and Apparatus for Securing Components Thereto," issued Aug. 2, 2016, and incorporated by reference herein.

II. Exemplary Rocker Arm Assembly

Figure 2:
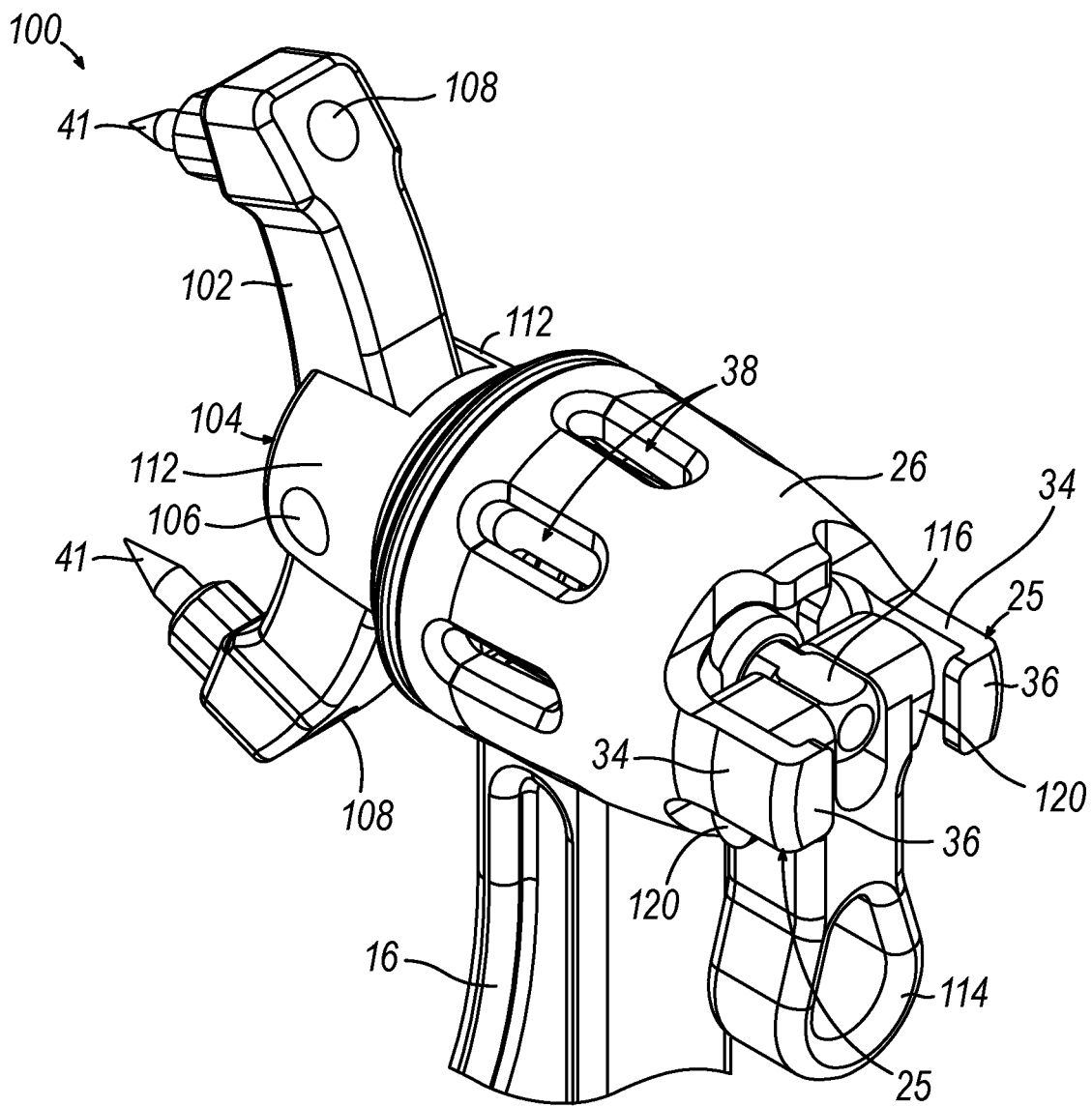
FIG. 2 depicts a perspective view of a rocker arm assembly connectable with the HFD of FIG. 1, shown with the rocker arm assembly in a locked or secured position or state.
Figure 3:
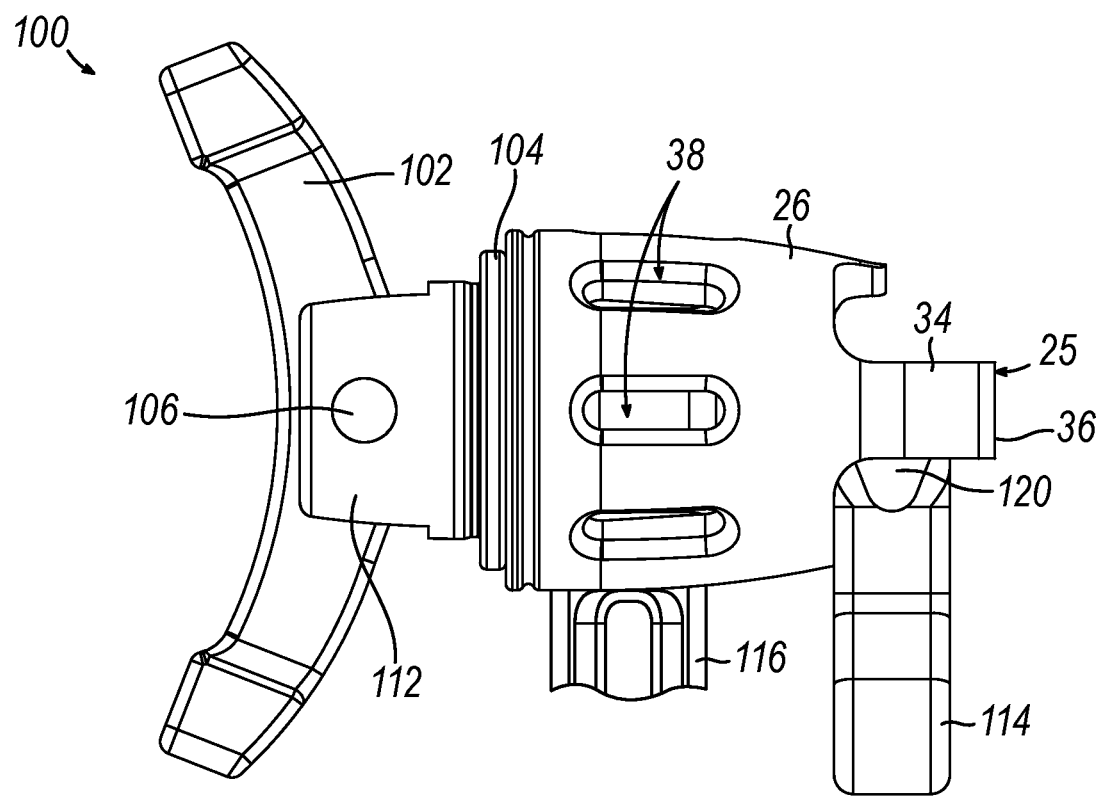
FIG. 3 depicts a side view of the rocker arm assembly of FIG. 2 connectable with the HFD of FIG. 1.

FIGS. 2 and 3 depict detailed views of rocker arm assembly (100) retained within housing (26) of skull clamp (10). Rocker arm assembly (100) includes rocker arm (102) and arm holder (104). In some instances, arm holder (104) can be referred to herein as a body (104). Rocker arm (102) and arm holder (104) connect by way of a pin (106). In the present example, but not required in all versions, rocker arm (102) is rotatable about pin (106) such that arm (102) can pivot relative to arm holder (104). In this manner, arm holder (104) includes a pair of extensions (112) that extend along each side of rocker arm (102). Extensions (112) and rocker arm (102) include aligned bores that receive pin (106). In some other versions, arm (102) can be fixed relative to arm holder (104) such that a pivotable adjustment is omitted.

As seen in FIG. 3, arm holder (104) is positioned adjacent to and in contact with housing (26). In this manner, arm holder (104) includes a proximal surface or flange (110) that is adjacent to and/or contacts a distal surface (27) of housing (26). Rocker arm (102) also includes bores (108) that are each configured to receive a stabilizing feature as described above. In the present example, rocker arm (102) has an arcuate or curved shape; however, in other examples rocker arm (102) could have a different shape such as straight, angled, bent, among others. In view of the teachings herein, other ways to configure rocker arm (102) and arm holder (104) will be apparent to those of ordinary skill in the art.

On a proximal side, rocker arm assembly (100) includes an actuator in the form of a lever (114). Lever (114) connects with a shaft (116) at a proximal end of shaft (116) by way of a pin (118) as best seen in FIG. 8. Lever (114) includes a pair of eccentric features (120), which in the present example are positioned near or adjacent to housing (26). More specifically, housing (26) includes extensions (25) that extend proximally past eccentric features (120) of lever (114). Furthermore, each extension (25) includes a longitudinal portion (34) and a lateral portion (36) that extends orthogonally relative to longitudinal portion (34). As will be explained in detail below, when operating lever (114), eccentric features (120) are configured to contact lateral portions (36) of extensions (25) of housing (26).

As will be described further below, this contact when operating lever (114) enables adjustment of a rotational position of rocker arm assembly (100). Additionally, with the interface between arm holder (104) and housing (26) defined by two contacting smooth surfaces—proximal surface (110) of arm holder (104) and distal surface (27) of housing (26)—rocker arm (102) can be rotatably adjusted to any desired position. In other words, the range of rotatable adjustment of rocker arm (102) is not limited as it might be where a gear engagement like teeth of a starburst interface would dictate rotational position and permitted increments of rotation. In the present version, any rotational increment and any rotational position from 0 degrees to 360 degrees about a longitudinal axis of rotation is achievable. In some versions, the range of adjustment of rocker arm (102) is infinitely variable, meaning that there is no restriction or limit as to the rotational position rocker arm (102) may be set to within its full range of rotation about longitudinal axis (LA).

As illustrated in FIGS. 2 and 3, housing (26) includes a plurality of elongated openings (38) that provide access to bore (28) of housing from an exterior sidewall of housing (26). In some instances, openings (38) are configured to provide access for improved cleaning and/or sterilization. In some other versions, housing (26) may be configured without openings (38) such that housing (26) has a continuous sidewall that may be smooth or textured.

Figure 4:
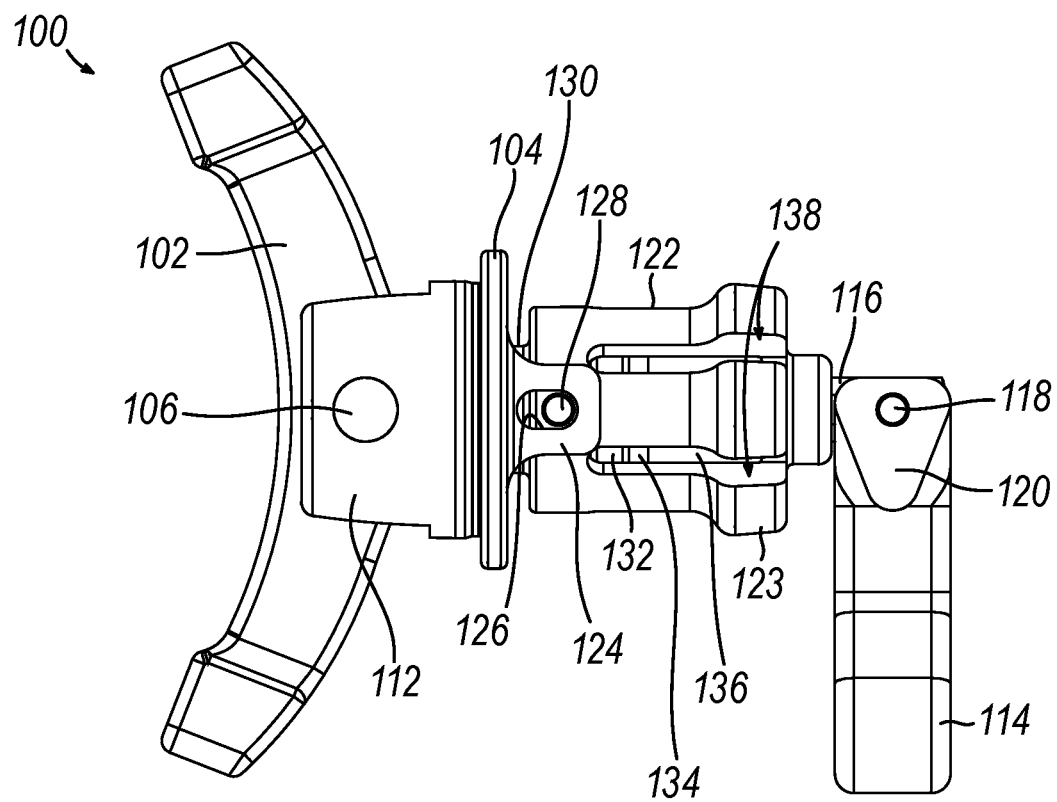
FIG. 4 depicts a side view of the rocker arm assembly of FIG. 3, shown separate from the HFD of FIG. 1.

FIG. 4 depicts rocker arm assembly (100) separate from housing (26) of skull clamp (10). As shown, rocker arm assembly (100) includes body (122). Body (122) connects with arm holder (104). More specifically, in the present example arm holder (104) includes extensions (124) on each side. Extensions (124) each have an elongated opening (126). Extensions (124) and their elongated openings (126) overlap with body (122). Body (122) includes a bore that aligns with elongated openings (126). A pin (128) extends through elongated openings (126) of arm holder (104) and bore of body (122) connecting body (122) and arm holder (104). With the elongated nature of elongated openings (126), the connection between arm holder (104) and body (122) is configured such that body (122) may translate relative to arm holder (104) and without causing corresponding translation of arm holder (104), at least over the distance represented by the difference between the diameter of pin (128) and the length of elongated opening (126). This movement will be described in further detail below with reference to FIGS. 8 and 9.

As will be described in detail below with respect to FIGS. 8 and 9, rocker arm assembly (100) also includes an insert (130). Insert (130) is connectable with body (122) and arm holder (104) also via pin (128). Insert (130) extends distally towards arm holder (104) such that a portion of insert (130) is received by a space or recess (105) within arm holder (104). Insert (130) also extends proximally towards lever (114) such that a portion of insert (130) resides within a space of body (122). Again, further illustration and description of insert (130) is provided below.

Figure 9:
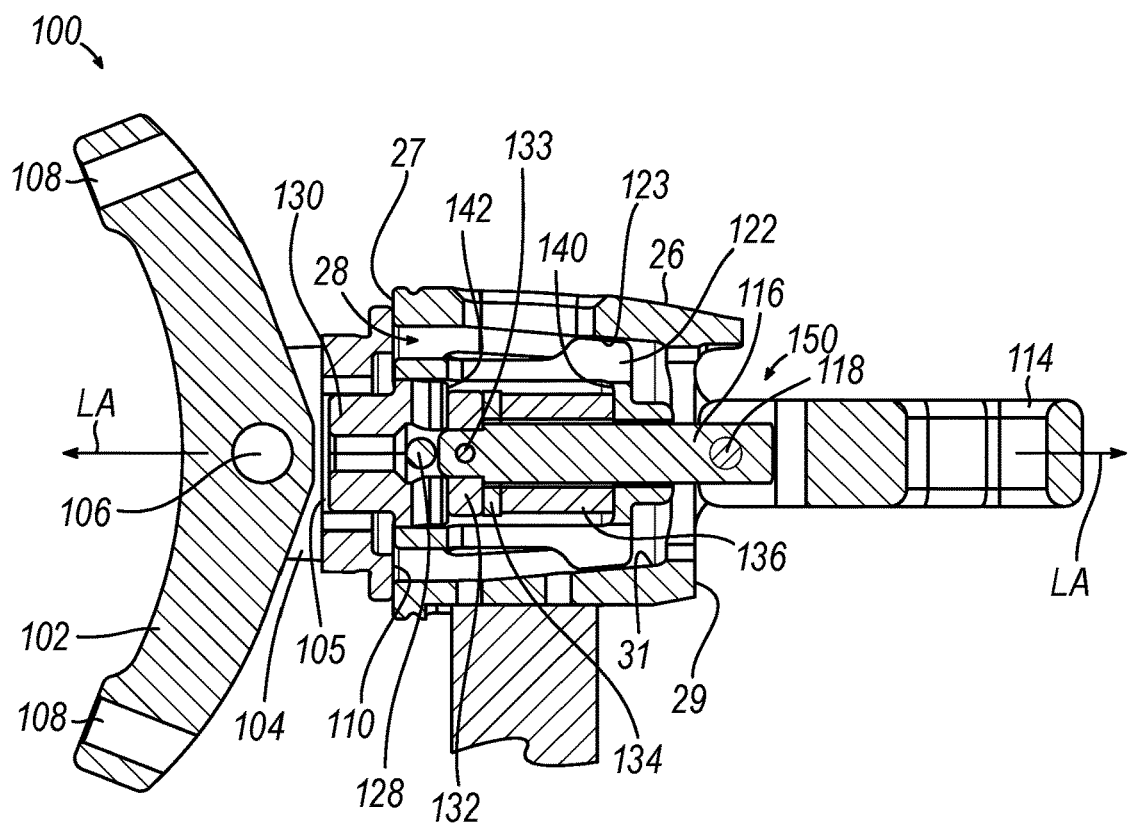
FIG. 9 depicts a side view in cross section of the rocker arm assembly of FIG. 5 connectable with the HFD of FIG. 1.

Rocker arm assembly (100) also includes a disc (132), a washer (134), and a resilient member or feature (136), as more clearly seen in FIGS. 8 and 9. Disc (132) is positioned about shaft (116) and is connected with shaft (116) by way of a pin (133) as seen in FIG. 8. Washer (134) is also positioned about shaft (116) and is located proximal of disc (132). Resilient member (136) is also positioned about shaft (116) and is located proximal of washer (134). At a proximal side of rocker arm assembly (100), resilient member (136) abuts or contacts an inner wall (140) of body (122) as seen in FIG. 8, while shaft (116) extends proximally through an opening in the proximal end of body (122). Shaft (116) connects with lever (114) proximal to body (122) as described above. Further illustration and description of disc (132), washer (134), and resilient member (136) is provided below.

In the illustrated version seen in FIG. 4, body (122) also includes a plurality of elongated openings (138) that provide access to an interior of body (122) from an exterior sidewall of body (122). In some instances, openings (132) are configured to provide access for improved cleaning and/or sterilization. In some other versions, body (122) may be configured without openings (138) such that body (122) has a continuous sidewall that may be smooth or textured.

Figure 5:
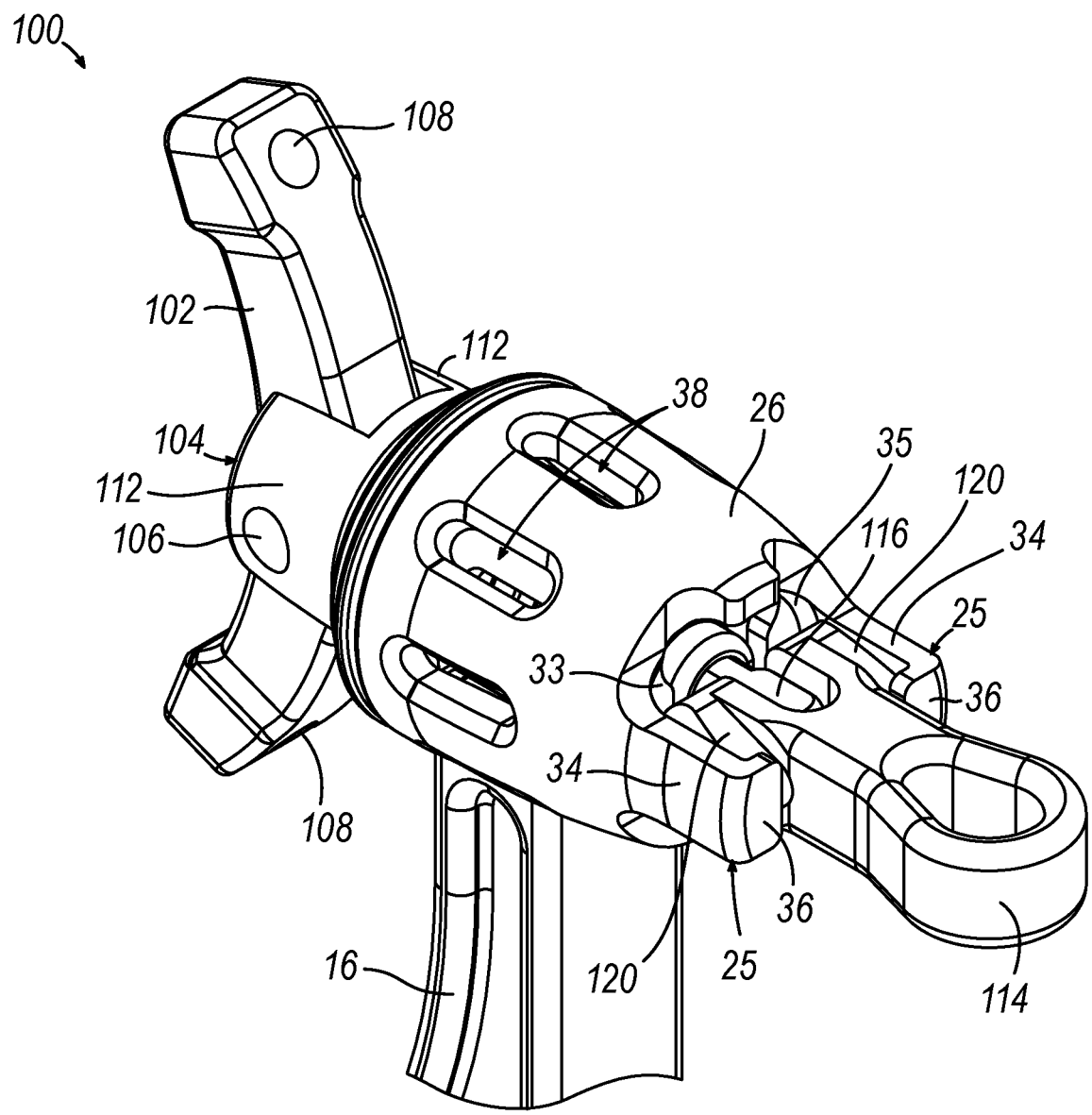
FIG. 5 depicts a perspective view of the rocker arm assembly of FIG. 2 connectable with the HFD of FIG. 1, shown with the rocker arm assembly in an unlocked or adjustable position or state.
Figure 6:
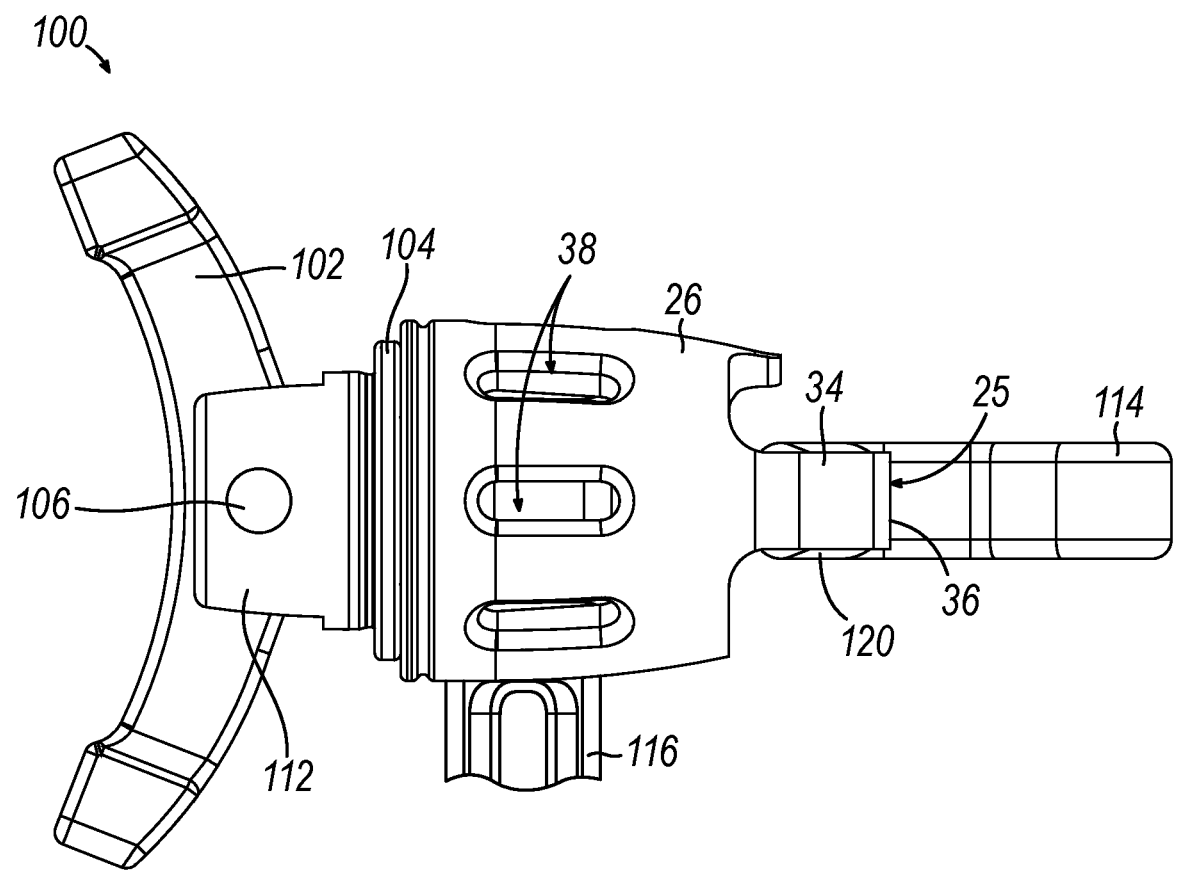
FIG. 6 depicts a side view of the rocker arm assembly of FIG. 5 connectable with the HFD of FIG. 1.
Figure 7:
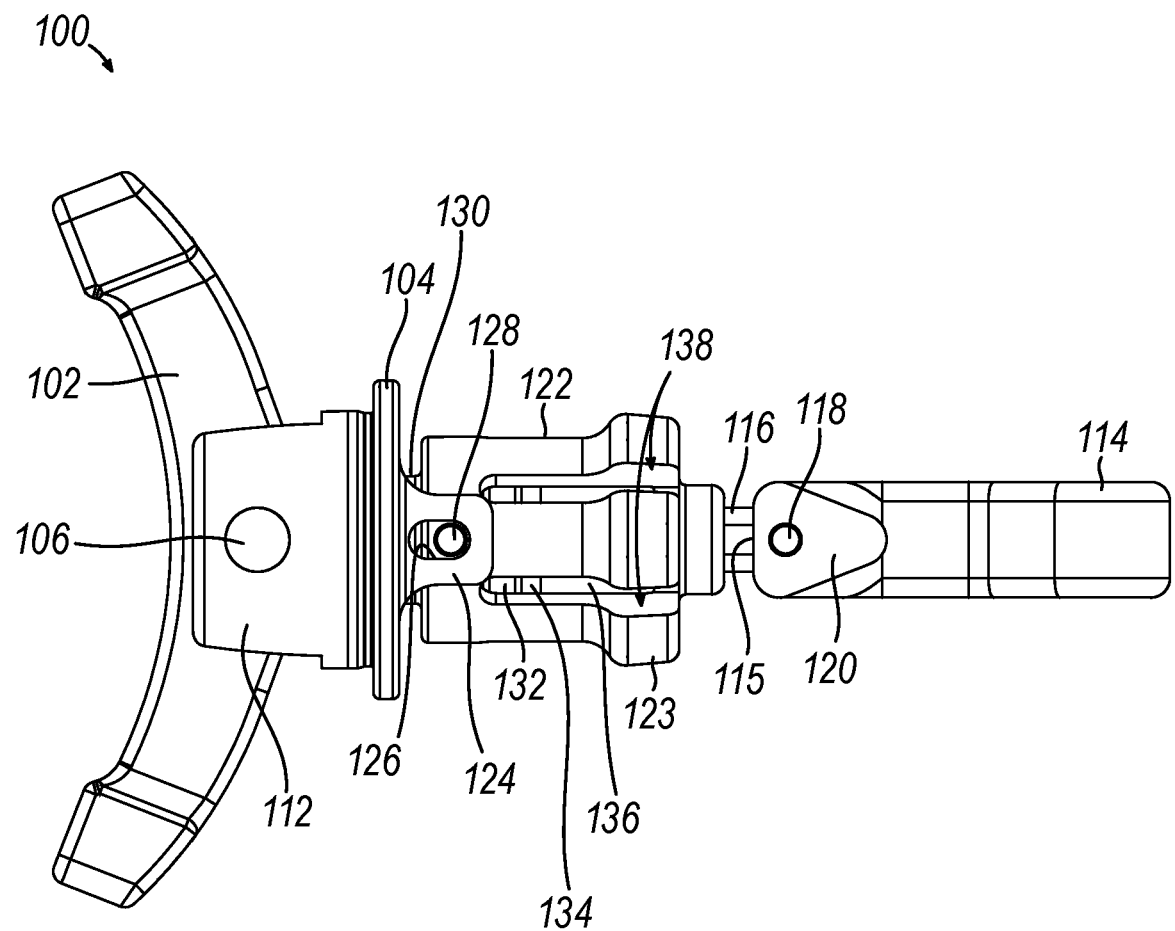
FIG. 7 depicts a side view of the rocker arm assembly of FIG. 6, shown separate from the HFD of FIG. 1.

FIGS. 5-7 depict views of rocker arm assembly (100) similar to the views shown in FIGS. 2-4. However, in FIGS. 2-4, rocker arm assembly (100) is shown in the locked or fixed state or position where rocker arm (102) is fixed rotationally or non-adjustable rotationally. In contrast, FIGS. 5-7 illustrate rocker arm assembly (100) in the unlocked or adjustable state or position where rocker arm (102) is rotatably adjustable about a longitudinal axis of rocker arm assembly (100).

As shown, in the locked state of FIGS. 2-4, lever (114) is rotated to a position that is orthogonal to a longitudinal axis of rocker arm assembly (100). In the present example, shaft (116) defines a longitudinal axis (LA) of rocker arm assembly (100) as shown in FIG. 8. In the unlocked state of FIGS. 5-7, lever (114) is rotated to a position that is parallel with or substantially parallel with longitudinal axis (LA).

Referring now to FIGS. 8 and 9, the locked and unlocked, or fixed and adjustable, states or positions of rocker arm assembly (100) will be described in further detail. FIG. 8 illustrates the locked position, while FIG. 9 illustrates the unlocked position. Again, in the locked position, rocker arm (102) is not rotatably adjustable, whereas in the unlocked position, rocker arm (102) is rotatably adjustable. Referring to FIG. 8, lever (114) is oriented orthogonal to longitudinal axis (LA). In this position, lever (114) contacts a proximal surface (29) of housing (26). Fixed to lever (114) is shaft (116) via pin (118) as mentioned above, which is at a proximal end of shaft (116). At a distal end of shaft (116), disc (132) is connected via pin (133) as mentioned above. With lever (114) fixed in its longitudinal position by its contact with proximal surface (29) of housing (26), the position of disc (132) is also fixed longitudinally when rocker arm assembly (100) is in the locked state or position.

As also mentioned above, washer (134) and resilient member (136) are located about shaft (116) and between disc (132) inner wall (140) of body (122). Resilient member (136) is configured in a compressed or loaded state such that when positioned about shaft (116), resilient member (136) is biased to apply force longitudinally on adjacent components or structures. In the present example, resilient member (136) applies force or pushes on adjacent washer (134) and on inner wall (140) of body (122). Because disc (132) is pinned to shaft (116) and in a fixed longitudinal position when lever (114) is locked or in a locked state as shown in FIG. 8, the force applied to washer (134) and adjacent disc (132) by resilient member (136) does not alter the position of disc (132) and connected shaft (116).

On the proximal side of resilient member (136), resilient member (136) contacts inner wall (140) of body (122). Body (122) is not fixedly connected with shaft (116) or components positioned about shaft (116). Body (122) is also not pinned or mechanically fastened with housing (26). Thus body (122) can translate longitudinally or change its longitudinal position relative to shaft (116) and housing (26) when force acts upon body (122). In the locked state shown in FIG. 8, the force imparted on inner wall (140) of body (122) by resilient member (136) causes body (122) to move or translate longitudinally in the proximal direction toward lever (114). As body (122) is driven proximally, an outer sidewall portion (123) of body (122) contacts and engages with an inner sidewall (31) of housing (26) making an interference fit that prevents body (122) from being rotatable relative to housing (26). This interference fit represents a fastening between body (122) and housing (26) where these components are fixed relative to one another by frictional forces between them such that body (122) does not rotate relative to housing (26). Accordingly, this type of interference fit can also be considered a press fit or friction fit.

In the present example, inner sidewall (31) of housing (26) is configured with a taper as it extends proximally such that a diameter of bore (28) of housing (26) decreases as bore (28) extends further proximally. Also in the present version, but not required in all versions, outer sidewall (123) of body (122) comprises a taper as well. In some versions the tapers of inner sidewall (31) and outer sidewall (123) match or are complementary; in other versions inner sidewall (31) tapers more severely or drastically than outer sidewall (123). Still in other versions outer sidewall (123) may not have any taper, while inner sidewall (31) may have a taper. In this manner, these configurations promote or define the interference fit made when outer sidewall portion (123) of body (122) contacts and engages with inner sidewall (31) of housing (26).

In the present example, when in the locked state and with body (122) moved proximally, body (122) contacts and engages inner sidewall (31) of housing (26) making an interference fit such that body (122) is restricted from rotational movement as mentioned above. Body (122) also connects with arm holder (104) via pin (128) as mentioned above. In this manner, when body (122) is restricted from rotational movement, arm holder (104) and connected rocker arm (102) are similarly restricted from rotational movement. In view of the teachings herein, other way to achieve an interference fit between body (122) and housing (26), where frictional forces fix the position of these components with respect to one another such that body (122) does not rotate relative to housing (26), will be apparent to those of ordinary skill in the art.

Rocker arm assembly (100) also includes insert (130) as mentioned above. Insert (130) is also connected with body (122) via pin (128). In this manner, when body (122) is restricted from rotational movement, insert (130) is similarly restricted from rotational movement. As shown in FIG. 8, insert (130) includes a distal portion that extends within recess (105) of arm holder (104). In the present example, recess (105) and the distal portion of insert (130) have complementary shapes such that recess (105) is specifically shaped to receive the shape of the distal portion of insert (130). A proximal portion of insert (130) extends within a space of body (122) and includes a bore that receives pin (128) for connecting insert (130) with body (122) and with arm holder (104).

From the above description, rocker arm assembly (100) is understood to include a locking assembly (150) that includes lever (114), pin (118), shaft (116), disc (132), pin (133), washer (134), and resilient member (136). Locking assembly (150) works in conjunction with body (122), insert (130), arm holder (104), and connecting pin (128) to selectively lock and unlock the rotation ability of arm (102) relative to housing (26). While body (122), insert (130), and arm holder (104) are connectable and are translatable relative to housing (26), housing (26) itself is formed with or fixedly connected with upright portion (16) of arm (12).

Referring now to FIG. 9, rocker arm assembly (100) is shown in the unlocked position. In this configuration or state, lever (114) is parallel with, or substantially parallel with, longitudinal axis (LA). In this position or orientation, eccentric features (120) of lever (114) rotate with lever (114) and contact lateral portions (36) of respective extensions (25). As seen in FIGS. 4 and 7, eccentric features (120) in the present example have an isosceles triangular shape with rounded ends where the triangular shape has two equal legs and a shorter base. Pin (118) passes through lever (114) and eccentric features (120) close to the base of the isosceles triangular shaped eccentric features (120). When lever (114) is rotated to the unlocked position of FIG. 9, eccentric features (120) extend proximally and contact lateral portions (36) of extensions (25). When lever (114) is rotated to the locked position of FIG. 8, eccentric features (120) no longer contact lateral portions (36). In view of the teachings herein, other shapes and configurations for eccentric features (120) will be apparent to those of ordinary skill in the art.

As mentioned above, when starting from the locked position or state as shown in FIG. 8, rotating lever (114) causes eccentric features (120) contact lateral portions (36) of extensions (25). With extensions (25) being part of housing (26), and with housing (26) fixed to upright portion (16) of arm (12), the contact between eccentric features (120) and lateral portions (36) causes locking assembly (150) to translate distally. In other words, actuation of locking assembly (150) provides a camming action where rotational movement of lever (114) produces translational movement of locking assembly (150) as a whole. With this motion, disc (132) contacts a proximal surface (142) of insert (130), and pushes insert (130) distally toward arm (102). As seen in FIGS. 8 and 9, recess (105) of arm holder (104) is configured with adequate space so that insert (130) is free to translate longitudinally in this manner, and further that such translation of insert (130) does not cause arm holder (104) to translate in unison with insert (130).

With the distal movement of insert (130), body (122) translates in unison with insert (130) based upon the pinned connection between insert (130) and body (122) via pin (128). It should be noted here that although resilient member (136) has a bias that drives body (122) proximally as describe above, the interaction between eccentric features (120) and lateral portions (36) of extensions (25) is sufficient to overcome the bias of resilient member (136). When body (122) translates distally, the interference fit between outer sidewall (123) of body (122) and inner sidewall (31) of housing (26) is lessened or reduced. In this manner, body (122) does not bind with housing (26), and body (122) is rotatable relative to housing (26).

Referring to FIGS. 4 and 7, extensions (124) of arm holder (104) have elongated opening (126) configured to receive pin (128) as mentioned above. Because of the shape of elongated opening (126) and the presence of recess (105) of arm holder (104), when locking assembly (150) translates distally when rocker arm assembly (100) is moved to the unlocked state of FIG. 9, pin (128) translates within the space of elongated opening (126). This configuration of arm holder (104) allows arm holder (104) to maintain its longitudinal position relative to housing (26) as can be seen in the comparison of views in FIGS. 8 and 9. For instance, as shown arm holder (104) comprises proximal surface or flange (110) that is positioned adjacent to housing (26) such that proximal surface (110) contacts distal surface (27) of housing (26) in both the locked and unlocked states shown in FIGS. 8 and 9 respectively.

Even with the stable longitudinal position of arm holder (104) relative to housing (26), the ability for arm holder (104) to rotate is associated with the ability of body (122) to rotate based on the pinned connection between arm holder (104) and body (122) by pin (128). Therefore, when body (122) is in the proximal position as shown in FIG. 8 in the locked state, body (122) cannot rotate freely based on the interference fit as mentioned above; and thus, neither can arm holder (104) and connected arm (102). On the other hand, when body (122) is in the distal position as shown in FIG. 9 in the unlocked state, body (122) can rotate freely as mentioned above; and thus, arm holder (104) and connected arm (102) can also rotate freely.

Once arm (102) has been rotated and adjusted to a desirable position, rocker arm assembly (100) can be moved back to the locked state or position as shown in FIGS. 1-4 and 8. In this manner, rotating lever (114) such that it is orthogonal to longitudinal axis (LA), returns rocker arm assembly (100) to the locked position where arm (102) is no longer rotationally adjustable. This movement of lever (114) causes shaft (116) to retract or translate proximally. This action further causes disc (134) to translate proximally in unison with shaft (116), and by this movement, disc (134) ceases or lessens the force it applies to insert (130). This movement of disc (134) and the proximal bias of resilient member (136) mentioned above, causes resilient member (136) to apply a proximal force to body (122) at inner wall (140) causing body (122) to translate longitudinally in the proximal direction. As mentioned above, the rotational locking of body (122) is achieved by the interference fit between outer sidewall (123) of body (122) and inner sidewall (31) of housing (26).

Figure 10:
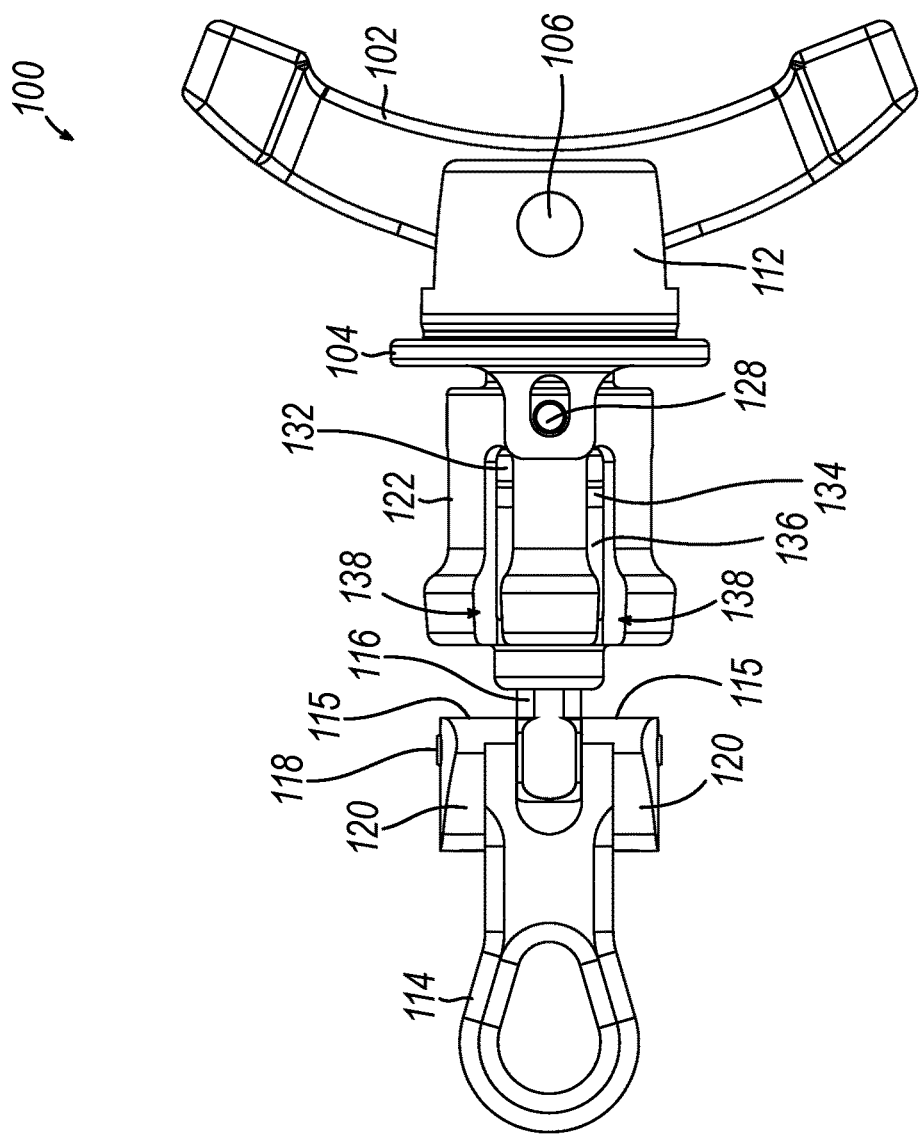
FIG. 10 depicts a partially exploded side view, showing the rocker arm assembly of FIG. 4 removed from a housing of the HFD of FIG. 1.
Figure 10:
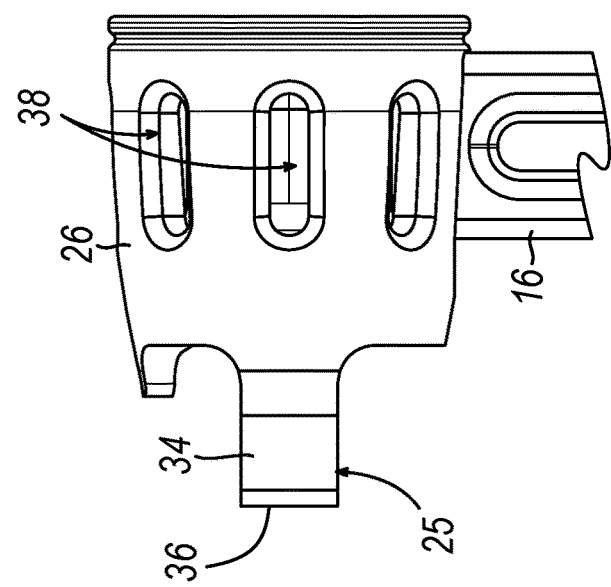

FIG. 10 depicts rocker arm assembly (100) removed from housing (26) of skull clamp (10). In the present example, rocker arm assembly (100) is removable from skull clamp (10) only from one side of housing (26). Furthermore, the one side from which rocker arm assembly (100) is removeable from skull clamp (10) is the distal side. As will be described below, rocker arm assembly (100) is removed from housing (26) by rotating locking assembly (150) and then pushing rocker arm assembly (100) distally such that lever (114) travels through bore (28) of housing (26) until exiting housing (26) on the distal side of housing (26).

Referring back to FIG. 5, housing (26) includes proximal wall portions (33, 35) that protrude or extend inward toward longitudinal axis (LA). Lever (114), when in the position shown in FIG. 5, is shaped and sized such that base portions (115) of lever (114) on each of eccentric features (120) (as best seen in FIG. 7) abut respective wall portions (33, 35). In this manner, wall portions (33, 35) act as a stop such that lever (114) cannot advance distally through bore (28) of housing (26).

Figure 11:
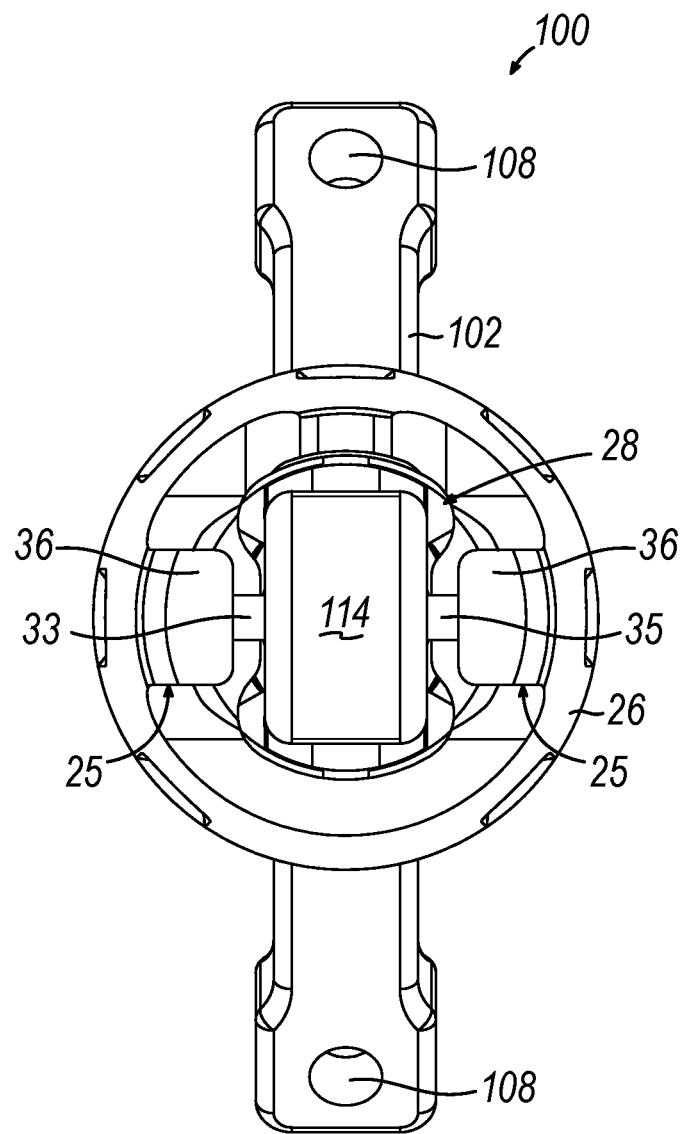
FIG. 11 depicts an end view of the rocker arm assembly of FIG. 5 connectable with the HFD of FIG. 1, showing the actuator rotated ninety degrees in preparation for removing the rocker arm assembly from the HFD.

FIG. 11 depicts an end view where lever (114) has been rotated 90 or 270 degrees in preparation to remove rocker arm assembly (100) from housing (26). As shown, rotating lever (114) allows base portions (115) to no longer abut wall portions (33, 35) and further have clearance from wall portions (33, 35) such that lever (114) can advance distally through bore (28) of housing (26). In this manner, housing (26) is configured with a proximal opening configured to receive lever (114) in a first position, but also configured to maintain lever (114) proximal to this opening when lever (114) is in a second position. To remove rocker arm assembly (100) from housing (26), once lever (114) has been rotated to the position shown in FIG. 11, the user can advance rocker arm assembly (100) distally by pushing lever (114) through bore (28) of housing (26) until rocker arm assembly (100) is separate from housing (26) as shown in FIG. 10.

With the configuration of rocker arm assembly (100) described, another feature of rocker arm assembly (100) is that removal of rocker arm assembly (100) from housing (26) does not require all components of rocker arm assembly (100) to be rotated 90 or 270 degrees like lever (114) to achieve removal. For instance, locking assembly (150) is rotatable independent from body (122), arm holder (104), and insert (130). Accordingly, when removing rocker arm assembly (100) from housing (26), locking assembly (150) is rotated based on rotation of lever (114), but the other components of rocker arm assembly (100) are not required to rotate and thus can remain stationary in terms of their relative rotational position with respect to housing (26).

To reinstall rocker arm assembly (100) within housing (26), the same process is performed in reverse. Once rocker arm assembly (100) has been reinstalled or repositioned within housing (26) with lever (114) extending proximally from wall portions (33, 35) of housing (26), lever (114) is rotated 90 or 270 degrees to the orientation as shown in FIGS. 5-7 such that base portions (115) of lever (114) again abut wall portions (33, 35) of housing. In this configuration, rocker arm assembly (100) cannot be advanced distally through housing (26) and separated therefrom.

The ability to separate rocker arm assembly (100) from HFD (10) in the manner as described above provides for the ability to clean and/or sterilize components of both rocker arm assembly (100) and HFD (10) such that these devices can be used multiple times. In view of the teachings herein, other ways to configure housing (26) and rocker arm assembly (100) to facilitate selective removal of rocker arm assembly (100) from HFD (10) will be apparent to those of ordinary skill in the art.

In an exemplary use of HFD (10) equipped with rocker arm assembly (100) where a user adjusts a rotational position of arm (102), a user first rotates lever (114) to a position parallel or substantially parallel with longitudinal axis (LA). Next the user rotates arm (102) to a desired orientation or position relative to housing (26). Once in the desired position, the user then rotates lever (114) to a position orthogonal to longitudinal axis (LA). When the user desires to remove rocker arm assembly (100) from housing (26) for cleaning or other reasons, the user rotates lever (114) to a position parallel or substantially parallel with longitudinal axis (LA). Next the user rotates lever (114) about longitudinal axis (LA) 90 or 270 degrees such that base portions (115) of lever (114) are clear from wall portions (33, 35) of housing (26). The user then advances rocker arm assembly (100) distally such that lever (114) passes through bore (28) of housing (26) and out from the distal side of housing (26). To reinstall rocker arm assembly (100), the reverse process is followed by the user. In view of the teaching herein, other ways to use and adjust rocker arm assembly (100) will be apparent to those of ordinary skill in the art.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. The following examples are being provided for nothing more than merely illustrative purposes. It is contemplated that the various teachings herein may be arranged and applied in numerous other ways. It is also contemplated that some variations may omit certain features referred to in the below examples.

EXAMPLE 1

An apparatus, for use with a head fixation device having a housing, is configured to retain and position one or more stabilizing features. The apparatus comprises an arm configured to retain the one or more stabilizing features. The arm is rotatable relative to the housing of the head fixation device to adjust position of the one or more stabilizing features. The apparatus also comprises a locking assembly connected with the arm. The locking assembly is configured to selectively secure the arm relative to the housing of the head fixation device by moving between a locked state and an unlocked state. In the locked state the rotatable position of the arm is fixed. In the unlocked state the rotatable position of the arm is adjustable. The locking assembly is configured such that the arm is selectively lockable at any rotational position about an axis of rotation defined by the locking assembly.

EXAMPLE 2

The apparatus of Example 1, wherein the locking assembly comprises a lever that is rotatable between two positions, wherein in a first position the locking assembly is in the locked state, and in a second position the locking assembly is in the unlocked state.

EXAMPLE 3

The apparatus of Example 2, wherein the first position of the lever is substantially orthogonal to the second position of the lever.

EXAMPLE 4

The apparatus of any one or more of Example 1 through Example 3, wherein the locking assembly comprises a resilient member configured to bias the locking assembly to a locked state.

EXAMPLE 5

The apparatus of any one or more of Example 2 through Example 4, wherein the locking assembly comprises a shaft connectable with the lever, wherein rotation of the lever relative to the shaft causes translation the shaft.

EXAMPLE 6

The apparatus of Example 5, wherein the shaft and the lever are connected by a pin, wherein rotation of the lever about an axis defined by the shaft causes corresponding rotation of the shaft.

EXAMPLE 7

The apparatus of any one or more of Example 5 through Example 6, wherein the locking assembly comprises a first body configured to contain the resilient member, wherein the shaft extends proximally from the first body and connects with the lever, wherein the resilient member biases the locking assembly to a locked state by driving the first body proximally.

EXAMPLE 8

The apparatus of Example 7, wherein the first body is selectively positioned within the housing of the head fixation device.

EXAMPLE 9

The apparatus of any one or more of Example 7 through Example 8 wherein the locking assembly comprises a second body configured to retain the arm, wherein the second body is connected with the first body.

EXAMPLE 10

The apparatus of any one or more of Example 2 through Example 9, wherein the lever comprises a feature configured to contact a portion of the housing to provide a camming action to the locking assembly.

EXAMPLE 11

The apparatus of Example 10, wherein the feature comprises an eccentric feature.

EXAMPLE 12

The apparatus of any one or more of Example 10 through Example 11, wherein the camming action overcomes the bias the resilient member places upon the first body to selectively permit adjustment of the rotational position of the arm relative to the housing.

EXAMPLE 13

The apparatus of any one or more of Example 5 through Example 12, wherein the shaft defines the axis of rotation of the locking assembly.

EXAMPLE 14

The apparatus of any one or more of Example 1 through Example 13, wherein the locking assembly is removable from the housing without disassembly of the apparatus.

EXAMPLE 15

The apparatus of any one or more of Example 2 through Example 14, wherein the lever is configured to fit through a proximal opening in the housing for removal of the locking assembly through a distal opening in the housing.

EXAMPLE 16

The apparatus of Example 15, wherein the lever is rotatable about a first and a second axis of rotation, wherein the lever is configured to fit through a proximal opening in the housing for removal of the locking assembly through a distal opening in the housing when the lever is rotated to a first position about the first axis of rotation and to a first position about the second axis of rotation.

EXAMPLE 17

The apparatus of any one or more of Example 7 through Example 16, wherein the first body comprises a plurality of slots around a perimeter of the first body, wherein the plurality of slots provide access to the locking assembly.

EXAMPLE 18

The apparatus of any one or more of Example 1 through Example 17, wherein the housing comprises a plurality of slots around a perimeter of the housing, wherein the plurality of slots provide access to a bore of the housing.

EXAMPLE 19

A head fixation device comprises a housing having a proximal opening, a distal opening, and a bore; and a stabilization assembly configured to retain one or more stabilizing features. A first portion of the stabilization assembly is received within the bore of the housing. A second portion of the stabilization assembly extends proximally from the proximal opening of the housing. A third portion of the stabilization assembly extends distally from the distal opening of the housing. The stabilization assembly is removable from the housing without disassembly of the stabilization assembly.

EXAMPLE 20

A method of removing a stabilization assembly from a housing of a head fixation device without disassembly of the stabilization assembly comprises: (a) locating the head fixation device with the stabilization assembly installed therein. The head fixation device comprises a housing having a proximal opening, a distal opening, and a bore. The stabilization assembly is configured to retain one or more stabilizing features. A first portion of the stabilization assembly is received within the bore of the housing, a second portion of the stabilization assembly extends from the proximal opening of the housing, and a third portion of the stabilization assembly extends from the distal opening of the housing; (b) moving an actuator of a locking assembly of the stabilization assembly from a first position to a second position; and (c) advancing the stabilization assembly longitudinally through the bore in the housing until the stabilization assembly exits the bore of the housing through a select one of the proximal opening and the distal opening. The stabilization assembly is maintained in an assembled state during removal of the stabilization assembly such that the stabilization assembly is removable as a single assembly.

EXAMPLE 21

A skull clamp for use to stabilize a head of a patient comprises: (a) a member having an upright portion and a lateral portion; (b) a housing formed with or connected to the upright portion, wherein the housing includes an opening extending from a first proximal side of the housing to a second distal side of the housing; (c) a stabilization assembly selectively connectable with the housing, wherein the stabilization assembly defines a longitudinal axis and comprises: (i) an arm configured to retain one or more stabilizing features, wherein the arm is selectively rotatable about the longitudinal axis, (ii) a locking assembly having a first position and a second position, wherein in the first position the locking assembly is configured to permit rotational adjustment of the arm about the longitudinal axis, and wherein in the second position the locking assembly is configured to fix the rotational position of the arm about the longitudinal axis such that the arm is not rotationally adjustable about the longitudinal axis, and (iii) a first body directly or indirectly connected with the arm and configured to rotate in unison with the arm, wherein the first body is in contact with the locking assembly, positioned within the opening of the housing, and longitudinally translatable within the housing, wherein the first body engages with the housing when the locking assembly is in the second position so that the rotational position of the arm is fixed.

EXAMPLE 22

The skull clamp of Example 21, wherein the locking assembly comprises (a) a shaft; and (b) a resilient member positioned about the shaft, wherein the resilient member is configured to bias the first body such that the first body impinges upon the housing to fix the rotational position of the arm.

EXAMPLE 23

The skull clamp of Example 22, wherein the locking assembly comprises an actuator connected with the shaft, wherein the actuator is configured to selectively overcome the bias imparted by the resilient member on the first body such that the arm is rotationally adjustable about the longitudinal axis of the rocker arm assembly.

EXAMPLE 24

The skull clamp of any one or more of Example 21 through Example 23, wherein the stabilization assembly comprises a second body connected with the arm, wherein the second body is further connected with the first body, and wherein first body, the second body, and the arm are selectively rotatably adjustable in unison.

EXAMPLE 25

The skull clamp of any one or more of Example 21 through Example 24, wherein the stabilization assembly comprises a rocker arm assembly.

EXAMPLE 26

The skull clamp of Example 23, wherein the actuator comprises a lever, wherein the lever comprises a feature configured to contact a portion of the housing to provide a camming action to overcome the bias the resilient member places upon the first body to selectively permit adjustment of the rotational position of the arm relative to the housing.

EXAMPLE 27

The skull clamp of Example 26, wherein the feature comprises an eccentric feature.

EXAMPLE 28

The skull clamp of any one or more of Example 21 through Example 27, wherein the arm remains fixed longitudinally relative to the housing.

EXAMPLE 29

The skull clamp of any one or more of Example 21 through Example 28, wherein the arm is selectively lockable in any rotational position about the longitudinal axis defined by the stabilization assembly.

EXAMPLE 30

The skull clamp of Example 24, wherein the second body comprises a pair of longitudinal extensions each having an elongated opening configured to receive a pin that passes through and further connects with the first body to join the first body and the second body.

EXAMPLE 31

The skull clamp of Example 21, wherein the stabilization assembly comprises a second body connected with the first body, wherein the second body translates longitudinally when the locking assembly is in the first position, wherein translation of the second body causes corresponding translation of the first body so that the rotational position of the arm is adjustable.

EXAMPLE 32

The skull clamp of any one or more of Example 21 through Example 31, wherein engagement of the first body with the housing comprises an outer sidewall portion of the first body contacting an inner sidewall of the housing to define an interference fit that prevents the first body from being rotatable relative to the housing.

EXAMPLE 33

The skull clamp of any one or more of Example 21 through Example 32, wherein engagement of the first body with the housing comprises moving the first body in a proximal direction.

EXAMPLE 34

The skull clamp of any one or more of Example 32 through Example 33, wherein the inner sidewall of the housing is configured with a taper as it extends proximally such that a diameter of a bore of the housing decreases as the bore extends further proximally.

EXAMPLE 35

The skull clamp of any one or more of Example 32 through Example 34, wherein the outer sidewall of the first body comprises a taper.

EXAMPLE 36

A skull clamp for use to stabilize a head of a patient comprises (a) an arm having an upright portion and a lateral portion; (b) a housing formed with or connected to the upright portion, wherein the housing includes an opening extending from a first proximal side of the housing to a second distal side of the housing; and (c) a rocker arm assembly selectively connectable with the housing. The rocker arm assembly comprises (i) a rocker arm configured to retain one or more stabilizing features, (ii) a first body connected with the rocker arm, wherein the first body and the rocker arm are selectively rotatably adjustable, (iii) a second body connected with the first body, wherein the second body is received within the housing and is translatable within the housing, (iv) a resilient member positioned within the second body, wherein the resilient member is configured to bias the second body such that the second body impinges upon the housing so that the first body and the rocker arm adopt a fixed state where the rocker arm is secure and not rotatably adjustable relative to the housing, (v) a shaft extending through the second body, and (vi) an actuator connected with the shaft, wherein the actuator is configured to selectively overcome the bias imparted by the resilient member on the second body such that the first body and the rocker arm are rotationally adjustable relative to the housing.

EXAMPLE 37

The skull clamp of Example 36, wherein the actuator comprises a lever, wherein the lever comprises an eccentric feature configured to contact a portion of the housing to provide a camming action to overcome the bias the resilient member places upon the second body to selectively permit adjustment of the rotational position of the first body and the rocker arm relative to the housing.

EXAMPLE 38

The skull clamp of any one or more of Example 36 through Example 37, wherein the first body remains fixed longitudinally relative to the housing.

EXAMPLE 39

The skull clamp of any one or more of Example 36 through Example 38, wherein the rocker arm is selectively lockable in any rotational position about an axis of rotation defined by rocker arm assembly.

EXAMPLE 40

The skull clamp of any one or more of Example 36 through Example 39, wherein the first body comprises a pair of longitudinal extensions each having an elongated opening configured to receive a pin that passes through and further connects with the second body to join the first body and the second body.

EXAMPLE 41

An apparatus for use with a head fixation device having a housing, wherein the apparatus is configured to retain and position one or more stabilizing features. The apparatus comprises an arm configured to retain the one or more stabilizing features. The arm is rotatable relative to the housing of the head fixation device to adjust position of the one or more stabilizing features. The apparatus further comprises a locking assembly connected with the arm, wherein the locking assembly is configured to selectively secure the arm relative to the housing of the head fixation device by moving between a locked state and an unlocked state. And the selectively lockable rotatable position of the arm for adjustment is infinitely variable about an axis of rotation defined by the locking assembly.

EXAMPLE 42

The apparatus of Example 41, wherein the locking assembly comprises a lever that is rotatable between two positions, wherein in a first position the locking assembly is in the locked state, and in a second position the locking assembly is in the unlocked state.

EXAMPLE 43

The apparatus of any one or more of Example 41 through Example 42, wherein the locking assembly comprises a resilient member configured to bias the locking assembly to a locked state.

EXAMPLE 44

The apparatus of any one or more of Example 42 through Example 43, wherein the locking assembly comprises a shaft connectable with the lever, wherein rotation of the lever relative to the shaft causes translation the shaft.

EXAMPLE 45

The apparatus of Example 44, wherein the shaft and the lever are connected by a pin, wherein rotation of the lever about an axis defined by the shaft causes corresponding rotation of the shaft.

EXAMPLE 46

The apparatus of any one or more of Example 44 through Example 45, wherein the locking assembly comprises a first body configured to contain the resilient member, wherein the shaft extends proximally from the first body and connects with the lever, wherein the resilient member biases the locking assembly to a locked state by driving the first body proximally.

EXAMPLE 47

The apparatus of Example 46, wherein the first body is selectively positioned within the housing of the head fixation device.

EXAMPLE 48

The apparatus of any one or more of Example 46 through Example 47 wherein the locking assembly comprises a second body configured to retain the arm, wherein the second body is connected with the first body.

EXAMPLE 49

The apparatus of any one or more of Example 42 through Example 48, wherein the lever comprises an eccentric feature configured to contact a portion of the housing to provide a camming action to the locking assembly.

EXAMPLE 50

The apparatus of Example 49, wherein the camming action overcomes the bias the resilient member places upon the first body to selectively permit adjustment of the rotational position of the arm relative to the housing.

EXAMPLE 51

The apparatus of any one or more of Example 41 through Example 50, wherein the locking assembly is removable from the housing from only one side of the housing.

EXAMPLE 52

The apparatus of any one or more of Example 42 through Example 51, wherein the lever is rotatable about a first and a second axis of rotation, wherein the lever is configured to fit through a proximal opening in the housing for removal of the locking assembly through a distal opening in the housing when the lever is rotated to a first position about the first axis of rotation and to a first position about the second axis of rotation.

IV. Miscellaneous

The components described herein may be constructed of a variety of material that will be apparent to those of ordinary skill in the art in view of the teachings herein. In one version, HFD (10) and/or rocker arm assembly (100) are constructed of radiolucent materials so as to provide no or limited artifacts during various imaging modalities. In other versions, HFD (10) and/or rocker arm assembly (100) are constructed from non-radiolucent materials. Such materials may include aluminum or various metal alloys among other non-metal materials.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for use with a head fixation device having a housing, wherein the apparatus is configured to retain and position one or more stabilizing features, the apparatus comprising:
   (a) an arm configured to retain the one or more stabilizing features, wherein the arm is rotatable relative to the housing of the head fixation device to adjust position of the one or more stabilizing features; and
   (b) a locking assembly connected with the arm, wherein the locking assembly is configured to selectively secure the arm relative to the housing of the head fixation device by moving between a locked state and an unlocked state, wherein in the locked state the rotatable position of the arm is fixed, wherein in the unlocked state the rotatable position of the arm is adjustable, wherein the locking assembly is configured such that the rotational position of the arm is selectively lockable at any rotational position about an axis of rotation defined by the locking assembly, wherein the locking assembly comprises a resilient member and a first body, wherein the resilient member biases the locking assembly to the locked state by driving the first body proximally.

2. The apparatus of claim 1, wherein the locking assembly comprises a lever that is rotatable between two positions, wherein in a first position the locking assembly is in the locked state and in a second position the locking assembly is in the unlocked state.

3. The apparatus of claim 2, wherein the locking assembly comprises a shaft connectable with the lever, wherein rotation of the lever relative to the shaft causes translation the shaft.

4. The apparatus of claim 2, wherein the lever is configured to fit through a proximal opening in the housing for removal of the locking assembly through a distal opening in the housing.

5. The apparatus of claim 4, wherein the lever is rotatable about a first and a second axis of rotation, wherein the lever is configured to fit through the proximal opening in the housing for removal of the locking assembly through the distal opening in the housing when the lever is rotated to a first position about the first axis of rotation and to a first position about the second axis of rotation.

6. The apparatus of claim 1, wherein the first body is configured to contain the resilient member, and wherein a shaft extends proximally from the first body and connects with a lever.

7. The apparatus of claim 6, wherein the locking assembly comprises a second body configured to retain the arm, wherein the second body is connected with the first body.

8. The apparatus of claim 6, wherein the lever comprises a feature configured to contact a portion of the housing to provide a camming action to the locking assembly.

9. The apparatus of claim 8, wherein the feature comprises an eccentric feature.

10. The apparatus of claim 8, wherein the camming action overcomes the bias the resilient member places upon the first body to permit adjustment of the rotational position of the arm relative to the housing.

11. The apparatus of claim 6, wherein the first body comprises a plurality of slots around a perimeter of the first body, wherein the plurality of slots provide access to the locking assembly.

12. The apparatus of claim 1, wherein the apparatus is removable from the housing without disassembly of the apparatus.

13. The apparatus of claim 1, wherein the housing comprises a plurality of slots around a perimeter of the housing, wherein the plurality of slots provide access to a bore of the housing.

14. A head fixation device comprising:
   (a) a housing having a proximal opening, a distal opening, and a bore; and
   (b) a stabilization assembly configured to retain two or more stabilizing features, wherein a first portion of the stabilization assembly is received within the bore of the housing, wherein a second portion of the stabilization assembly extends proximally from the proximal opening of the housing, wherein a third portion of the stabilization assembly extends distally from the distal opening of the housing, and wherein the stabilization assembly is removable from the housing without disassembly of the stabilization assembly.

15. A skull clamp for use to stabilize a head of a patient, wherein the skull clamp comprises:
   (a) a member having an upright portion and a lateral portion;
   (b) a housing formed with or connected to the upright portion, wherein the housing includes an opening extending from a first proximal side of the housing to a second distal side of the housing;
   (c) a stabilization assembly selectively connectable with the housing, wherein the stabilization assembly defines a longitudinal axis and comprises:
      (i) an arm configured to retain one or more stabilizing features, wherein the arm is selectively rotatable about the longitudinal axis,
      (ii) a locking assembly having a first position and a second position, wherein in the first position the locking assembly is configured to permit rotational adjustment of the arm about the longitudinal axis, and wherein in the second position the locking assembly is configured to fix the rotational position of the arm about the longitudinal axis such that the arm is not rotationally adjustable about the longitudinal axis, wherein the arm is selectively lockable in any rotational position about the longitudinal axis defined by the stabilization assembly, and (iii) a first body directly or indirectly connected with the arm and configured to rotate in unison with the arm, wherein the first body is in contact with the locking assembly, positioned within the opening of the housing, and longitudinally translatable within the housing to engage with the housing when the locking assembly is in the second position so that the rotational position of the arm is fixed by the engagement between the first body and the housing.

16. The skull clamp of claim 15, wherein the locking assembly comprises
(a) a shaft;
(b) a resilient member positioned about the shaft, wherein the resilient member is configured to bias the first body such that the first body impinges upon the housing to fix the rotational position of the arm; and
(c) an actuator connected with the shaft, wherein the actuator is configured to selectively overcome the bias imparted by the resilient member on the first body such that the arm is rotationally adjustable about the longitudinal axis of a rocker arm assembly.

17. The skull clamp of claim 16, wherein the actuator comprises a lever, wherein the lever comprises a feature configured to contact a portion of the housing to provide a camming action to overcome the bias the resilient member places upon the first body to selectively permit adjustment of the rotational position of the arm relative to the housing.

18. The skull clamp of claim 15, wherein engagement of the first body with the housing comprises an outer sidewall portion of the first body contacting an inner sidewall of the housing to define an interference fit that prevents the first body from being rotatable relative to the housing.

19. An apparatus for use with a head fixation device having a housing, wherein the apparatus is configured to retain and position one or more stabilizing features, the apparatus comprising:
(a) an arm configured to retain the one or more stabilizing features, wherein the arm is rotatable relative to the housing of the head fixation device to adjust position of the one or more stabilizing features; and
(b) a locking assembly connected with the arm, wherein the locking assembly is configured to selectively secure the arm relative to the housing of the head fixation device by moving between a locked state and an unlocked state, wherein in the locked state the rotatable position of the arm is fixed, wherein in the unlocked state the rotatable position of the arm is adjustable, wherein the locking assembly is configured such that the rotational position of the arm is selectively lockable at any rotational position about an axis of rotation defined by the locking assembly, wherein the apparatus is removable from the housing without disassembly of the apparatus.

20. An apparatus for use with a head fixation device having a housing, wherein the apparatus is configured to retain and position one or more stabilizing features, the apparatus comprising:
(a) an arm configured to retain the one or more stabilizing features, wherein the arm is rotatable relative to the housing of the head fixation device to adjust position of the one or more stabilizing features; and
(b) a locking assembly connected with the arm, wherein the locking assembly is configured to selectively secure the arm relative to the housing of the head fixation device by moving between a locked state and an unlocked state, wherein in the locked state the rotatable position of the arm is fixed, wherein in the unlocked state the rotatable position of the arm is adjustable, wherein the locking assembly is configured such that the rotational position of the arm is selectively lockable at any rotational position about an axis of rotation defined by the locking assembly, wherein the locking assembly comprises a lever that is rotatable between two positions, wherein in a first position the locking assembly is in the locked state and in a second position the locking assembly is in the unlocked state, wherein the lever is configured to fit through a proximal opening in the housing for removal of the locking assembly through a distal opening in the housing.

* * * * *